United States Patent [19]

Hlavka et al.

[11] Patent Number: 4,550,169

[45] Date of Patent: Oct. 29, 1985

[54] PLATINUM CHELATES OF 2-HYDRAZINO-AZOLES

[75] Inventors: Joseph J. Hlavka, Tuxedo; Panayota Bitha, Pomona; Yang-I Lin, Nanuet, all of N.Y.

[73] Assignee: American Cyanamid Company, Stamford, Conn.

[21] Appl. No.: 553,675

[22] Filed: Nov. 21, 1983

[51] Int. Cl.[4] ............................................. C07F 15/00
[52] U.S. Cl. ............................. 548/108; 260/239 BE; 544/225; 546/12; 548/109; 548/402
[58] Field of Search ................. 548/101, 108, 109, 402

[56] References Cited

U.S. PATENT DOCUMENTS 4,053,587 10/1977 Davidson et al. ................... 424/131
4,278,660 7/1981 Allcock et al. ....................... 424/78
4,457,926 7/1984 Amundsen et al. ................. 424/245

FOREIGN PATENT DOCUMENTS 2131020 6/1984 United Kingdom ................ 548/109

OTHER PUBLICATIONS

Uno, et al., J. Pharm. Soc. Japan, vol. 81, No. 4, pp. 585–590 (1961).
Doadrio, et al., Chemical Abstracts, vol. 96, 210435d (1982).
Bales, et al., Chemical Abstracts, vol. 98, 30650c (1983).
Melachen, et al., J. Nat'l. Cancer Inst., vol. 57, No. 4, 10/76, pp. 841–845.

*Primary Examiner*—Donald G. Daus
*Assistant Examiner*—Diana G. Rivers
*Attorney, Agent, or Firm*—Edward A. Conroy, Jr.

[57] ABSTRACT

This disclosure describes platinum chelates of 2-hydrazino-1-aza (or 1,3-diaza,1-oxa-3-aza or 1-thia-3-aza)-1-cyclo-alkenes which possess activity as antitumor agents.

9 Claims, No Drawings

PLATINUM CHELATES OF 2-HYDRAZINO-AZOLES

SUMMARY OF THE INVENTION

This invention relates to platinum chelates of new organic compounds and more particularly, is concerned with platinum chelates of 2-hydrazino-1H-imidazoles which my be represented by formula:

FORMULA I

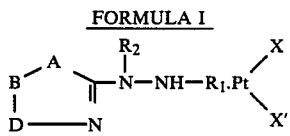

wherein $R_1$ is selected from the group consisting of hydrogen, alkyl($C_1$–$C_6$), trifluoroethyl and phenyl; $R_2$ is selected from the group consisting of hydrogen and alkyl ($C_1$–$C_6$); A is selected from the group consisting of

—S—, —O— and —CH$_2$—; $R_3$ is selected from the group consisting of hydrogen and 1-methylethanol; B and D taken together are selected from the group consisting of

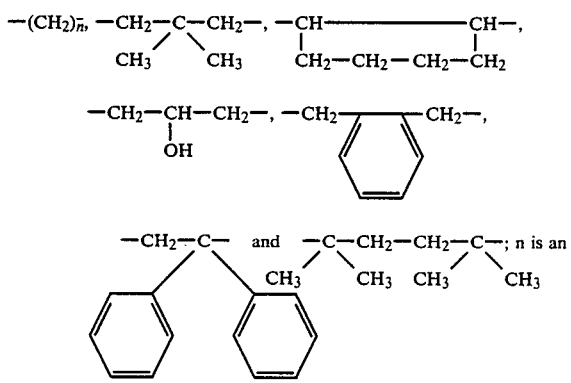

integer 2–7; and X and X' are the same or different and are selected from the group consisting of halide, nitrate, nitrite, thiocyanate, sulfate and a monobasic organic acid, such as glucuronic acid, or X and X' taken together may be a dibasic organic acid such as malonic acid, oxalic acid, methyl malonic acid, succinic acid or tartronic acid.

In addition this invention is concerned with a class of intermediates used to prepare the compounds of formula I, which intermediates may be represented by formula II:

FORMULA II

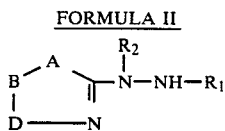

wherein $R_1$, $R_2$, A, B and D are as described above.

DESCRIPTION OF THE INVENTION

The intermediates of formula II may be prepared according to the following reaction scheme:

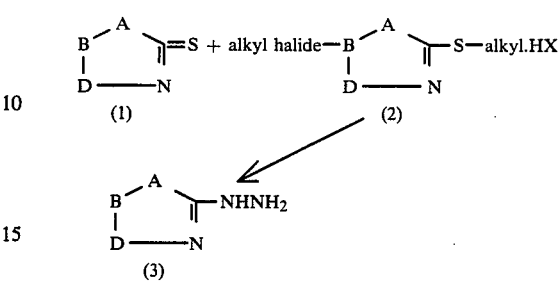

According to the above reaction scheme a substituted 2-thio-1H-1,3-diazepine (1), where A is

and B and D are described above, is reacted with an alkyl halide in ethanol at reflux for several hours, then cooled to below 0° C. giving a substituted 2-alkylthio-1H-1,3-diazepine hydrohalide (2) which is then reacted with hydrazine in ethanol, giving the intermediate 2-hydrazino-substituted-1H-1,3-diazepines (3) which are then reacted with potassium tetrachloroplatinate to obtain the products of this invention.

To prepare compounds of formula I where X and X' are nitro, compounds where X and X' are chloro are dissolved in water and reacted with two equimolar amounts of silver nitrate for several hours at room temperature, then filtered and the filtrate evaporated to give the dinitrate derivatives.

To obtain the organic acid derivatives the dinitrate compound is reacted with one equimolar amount of the potasium salt of a dibasic acid or two equimolar amounts of the potassium salt of a monobasic acid.

The novel chelated compounds of the present invention possess the property of inhibiting the growth of transplanted mouse tumors as established by the following test.

Lymphocytic leukemia P388 test

The animals used were BDF/1 mice all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9, relative to tumor inoculation, at various doses. The animals were weighed and survivors recorded on a regular basis for 30 days. The median survival time and the ratio of survival time for treated (T)/control (C) animals were calculated. The positive control compound was either 1,4-dihydroxy-5,8-bis[[2-(2-hydroxyethylamino)ethyl]amino]anthraquinone dihydrochloride or Cisplatin. The results of this test on representative compounds of this invention appear in Table I.

TABLE I

| Compound | Dose (mg/kg) | Median Survival (Days) | T/C × 100 (%) |
|---|---|---|---|
| 2-hydrazino-4,5-dihydro-4-phenyl-1H—imidazole, compound with platinum chloride iodide (1:1) | 200 | 13 | 113 |
| Control | — | 11.5 | — |
| Cisplatin | 1.25 | 20 | 174 |
|  | 0.6 | 25.5 | 222 |
| 2-hydrazino-4,5-dihydro-1H—imidazole, compound with platinum chloride (1:1) | 25 | 15.5 | 147 |
|  | 12 | 16 | 152 |
|  | 6 | 13 | 124 |
|  | 3 | 12 | 114 |
| Control | — | 10.5 | — |
| 1,4-dihydroxy-5,8-bis[[2-(2-hydroxyethylamino)ethyl]-amino]anthraquinone dihydrochloride | 1.6 | 21.5 | 205 |
|  | 0.4 | >29 | >276 |
|  | 0.1 | 24 | 228 |
|  | 0.025 | 17.5 | 167 |
| 7-hydrazino-3,4,5,6-tetrahydro-2H—azepine, compound with platinum chloride (1:1) | 50 | 18 | 171 |
|  | 12 | 17.5 | 167 |
|  | 3 | 13.5 | 129 |
| Control | — | 10.5 | — |
| Cisplatin | 1.25 | 14.5 | 138 |
|  | 0.6 | 15.5 | 148 |
| 2-hydrazino-3a,4,5,6,7,7a-hexahydro-1H—benzimidazole, compound with platinum chloride (1:1) | 200 | 16.5 | 143 |
|  | 50 | 15 | 130 |
| Control | — | 11.5 | — |
| Cisplatin | 1.25 | 20 | 174 |
|  | 0.6 | 25.5 | 222 |
| 4,5-dihydro-2-(1-methylhydrazino)-1H—imidazole, compound with platinum chloride (1:1) | 200 | 22 | 191 |
|  | 50 | 19.5 | 170 |
|  | 12 | 16.5 | 143 |
|  | 3 | 15.5 | 135 |
| Control | — | 11.5 | — |
| Cisplatin | 1.25 | 20 | 174 |
|  | 0.6 | 25.5 | 222 |
| 2,hydrazino-1,4,5,6-tetrahydropyrimidine, compound with platinum chloride (1:1) hydropyrimidine; 152 | 200 | 23.5 | 193 |
|  | 50 | 19.5 | 160 |
|  | 12 |  |  |
|  | 3 | 15.5 | 127 |
| Control | — | 12.2 | — |
| Cisplatin | 1.5 | 22.5 | 184 |
|  | 0.8 | 26.5 | 217 |
| 2-hydrazino-4,5,6,7-tetrahydro-1H—1,3-diazepine, compound with platinum chloride (1:1) | 12 | 18.5 | 165 |
|  | 6 | 18 | 161 |
|  | 3 | 17.5 | 156 |
|  | 1.5 | 15.5 | 138 |
|  | 0.8 | 14.5 | 129 |
| Control | — | 11.2 | — |
| Cisplatin | 2 | 20.5 | 183 |
|  | 1 | 17 | 152 |
|  | 0.5 | 14.5 | 129 |
| 2-hydrazino-1,4,5,6-tetrahydro-5,5-dimethylpyrimidine, compound with platinum chloride (1:1) | 12 | 18 | 161 |
|  | 6 | 17 | 152 |
|  | 3 | 16 | 143 |
|  | 1.5 | 15.5 | 138 |
|  | 0.8 | 16 | 143 |
| Control | — | 11.2 | — |
| Cisplatin | 2 | 20.5 | 183 |
|  | 1 | 17 | 152 |
|  | 0.5 | 14.5 | 129 |
| 2-hydrazino-1,4,5,6-tetrahydro-5-pyrimidinol, monohydrobromide, compound with platinum chloride (1:1) | 12 | 17.5 | 152 |
|  | 3 | 16.5 | 143 |
| Control | — | 11.5 | — |
| Cisplatin | 1.25 | 20 | 174 |
|  | 0.6 | 25.5 | 222 |
| 2-hydrazino-4,5-dihydro-α-methyl-1H—imidazole-1-ethanol, compound with platinum iodide (1:1) | 200 | 23 | 200 |
|  | 50 | 20 | 174 |
|  | 12 | 16.5 | 143 |
|  | 3 | 15 | 130 |
| Control | — | 11.5 | — |
| Cisplatin | 1.25 | 20 | 174 |
|  | 0.6 | 25.5 | 222 |
| 3-hydrazino-2,5-dihydro-1H—2,4-benzodiazepine, compound with platinum chloride iodide (1:1) | 200 | 17 | 170 |
|  | 50 | 13 | 130 |
|  | 12 | 12 | 120 |
|  | 3 | 10.5 | 105 |
| Control | — | 10 | — |
| Cisplatin | 1 | 21.5 | 215 |
|  | 0.5 | 19 | 190 |
| 2-hydrazino-4,5-dihydro-4,4-diphenyl-1H—imidazole, compound with platinum bromide choride (1:1) | 200 | 15.5 | 155 |
|  | 50 | 12 | 120 |
|  | 12 | 13 | 130 |
|  | 3 | 12.5 | 125 |
| Control | — | 10 | — |
| Cisplatin | 1 | 21.5 | 215 |
|  | 0.5 | 19 | 190 |
| 2-hydrazino-4,5,6,7-tetrahydro-4,4,7,7-tetramethyl-1H—1,3-diazepine, compound with platium chloride iodide (1:1) | 200 | 17.5 | 175 |
|  | 50 | 13.5 | 135 |
|  | 12 | 13 | 130 |
| Control | — | 10 | — |
| Cisplatin | 1 | 21.5 | 215 |
|  | 0.5 | 19 | 190 |
| 4,5-dihydro-2-(2-methylhydrazino)1H—imidazole, compound with platinum iodide (1:1) | 50 | 18 | 180 |
|  | 12 | 16.5 | 165 |
|  | 3 | 13 | 130 |
| Control | — | 10 | — |
| Cisplatin | 1 | 21.5 | 215 |
|  | 0.5 | 19 | 190 |
| 4,5-dihydro-2-[2-(2,2,2-trifluorethyl)hydrazino]-1H—imidazole compound with platinum iodide (1:1) | 200 | 13 | 127 |
|  | 50 | 11.5 | 113 |
|  | 12 | 11 | 108 |
|  | 3 | 10.5 | 103 |
| Control | — | 10.2 | — |
| Cisplatin | 2 | 21 | 206 |
|  | 0.5 | 17 | 167 |
|  | 0.12 | 13.5 | 132 |
| 2-hydrazino-3,4,5,6-tetrahydropyridine, compound with platinum chloride (1:1) | 50 | 26 | 255 |
|  | 12 | 19.5 | 191 |
|  | 3 | 14 | 137 |
| Control | — | 10.2 | — |
| Cisplatin | 2 | 27.5 | 270 |
|  | 1 | 22 | 216 |
|  | 0.5 | 20 | 196 |
|  | 0.25 | 17 | 167 |
| 7-(1-methylhydrazino)-3,4,5,6-tetrahydro-2H—azepine, compound with platinum chloride (1:1) | 200 | 19.5 | 191 |
|  | 50 | 15.5 | 152 |
|  | 12 | 13.5 | 132 |
|  | 3 | 13.5 | 132 |
| Control | — | 10.2 | — |
| Cisplatin | 2 | 27.5 | 270 |
|  | 1 | 22 | 216 |
|  | 0.5 | 20 | 196 |
|  | 0.25 | 17 | 167 |
| 5-hydrazino-3,4-dihydro-2H—pyrrole, compound with platinum chloride (1:1) | 12 | 24 | 224 |
|  | 6 | 24 | 224 |
|  | 3 | 20 | 187 |
| Control | — | 10.7 | — |
| Cisplatin | 1 | 21 | 196 |
|  | 0.5 | 21.5 | 201 |
|  | 0.25 | 16 | 150 |
| 5-hydrazino-3,4-dihydro-2H—pyrrole, compound with platinum iodide (1:1) | 25 | 28 | 267 |
|  | 12 | 22.5 | 214 |
|  | 6 | 15 | 143 |
|  | 3 | 14.5 | 138 |
| Control | — | 10.5 | — |
| Cisplatin | 3 | 18 | 171 |
|  | 1.5 | 15.5 | 148 |
|  | 0.8 | 13.5 | 129 |

This aspect of the invention includes the novel compositions of matter and the method of inducing the regression and/or palliation of leukemia and related cancers in mammals when administered in amounts ranging from about one mg to about 1.2 gm per square meter of body surface area per day. The interrelationship of dosages for animals of various sizes and species and humans (based on mg/m$^2$ of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219-244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds my be administered parenterally or intraperitoneally. Solutions or dispersions of the active compound can be prepared in water suitably mixed with a surfactant such as hydroxpropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micoorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignacies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

2-Hydrazino-2-imidazoline, dihydrochloride

A 50 g portion of 2-hydrazino-2-imidazoline hydrobromide was dissolved in 750 ml of hot absolute ethanol and treated with 100 ml of 6N hydrochloric acid in isopropanol. The precipitate was collected, washed with ethanol, dried, dissolved in 2300 ml of hot absolute ethanol, filtered and the filtrate treated with 6N hydrochloric acid in isopropanol, then cooled, giving 37 g of the desired intermediate, mp 185°-187° C.

EXAMPLE 2

2-Hydrazino-1,4,5,6-tetrahydropyrimidine

A reaction mixture comprising 119 g of 3,4,5,6-tetrahydro-2-pyrimidinethiol, 300 ml of ethanol, 100 ml of methanol and 100 ml of dimethylsulfate was warmed on a water bath with stirring for one hour. To this mixture was added dropwise 54.8 g of hydrazine hydrate with stirring and warming. After the addition was complete the mixture was heated at 60° C. for 1.5 hours. The mixture was evaporated to dryness and the residue crystallized from ethanol-isopropanol, giving 83.9 g of the desired intermediate, mp 145°–155° C.

EXAMPLE 3

2-Hydrazino-4,5,6,7-tetrahydro-1H-1,3-diazepine, hydrochloride

The procedure of A. F. McKay and M. E. Kreling, Can. J. Chem., 35 1438 (1957) was used to produce first 50.8 g of hexahydro-2H-1,3-diazepine-2-thione, mp 179°–180° C., and then 85 g of 4,5,6,7-tetrahydro-2-(methylthio)-1H-1,3-diazepine, hydroiodide.

A 38.5 g portion of 4,5,6,7-tetrahydro-2-(methylthio)-1H-1,3-diazepine, hydroiodide was slurried in 500 ml of water and 40 g of fresh silver chloride was added. The mixture was heated on a steam bath for 16 hours and then filtered. The filtrate was evaporated to dryness in vacuo, then dissolved in 150 ml of boiling ethanol. A 7 ml portion of hydrazine hydrate was added and the mixture was refluxed for 3 hours. The mixture was treated with charcoal, clarified, cooled to −10° C. and diluted with 150 ml of ether. The solid was collected, washed with ether and dried at 60° C. in vacuo, giving 19.4 g of the desired intermediate, mp 192°–193° C.

EXAMPLE 4

2-Hydrazino-1,4,5,6-tetrahydro-5,5-dimethylpyrimidine, hydrochloride

The commercially availble hydroidide salt was converted by treatment with hydrochloric acid in isopropanol to the desired intermediate, giving 7.15 g, mp 260°–265° C. (dec).

EXAMPLE 5

2-Hydrazino-α-methyl-2-imidazoline-1-ethanol, hydroiodide

A 100 g portion of (N-2-hydroxypropyl)ethylenediamine was dissolved in 500 ml of ethanol, then cooled to −10° C. and 55 ml of carbon disulfide was added. Another 500 ml of ethanol was added, the mixture was stirred 30 minutes and then the precipitate was collected, washed with ether and dried. This solid was heated at 140°–150° C. until hydrogen sulfide evolution ceased and then cooled to room temperature. The solid was dissolved in 500 ml of boiling water, treated with charcoal, clarified and cooled at 4° C. overnight. The solid was collected, washed with water and dried at 60° C. in vacuo, giving 34.1 g of 1-(2-hydroxypropyl)-2-imidazolidinethione mp 101°–102° C.

A solution composed of 32.0 g of 1-(2-hydroxypropyl)-2-imidazolidinethione, 250 ml of 2-propanol and 15 ml of methyliodide was stirred at reflux for 4 hours, then clarified, cooled at −10° C. and the solid collected, washed with 2-propanol, then ether and dried at 60° C. in vacuo, giving 52.7 g of α-methyl-2-(methylthio)-2-imidazoline-1-ethanol, hydroiodide, mp 114°–116° C.

A solution of 30.2 g of α-methyl-2-(methylthio)-2-imidazoline-1-ethanol, hydroiodide, 5.2 ml of hydrazine hydrate and 200 ml of 2-propanol was refluxed for 4 hours, clarified and cooled at −10° C. The solid was collected, washed with 100 ml of cold 2-propanol, then 200 ml of ether and dried at 60° C. in vacuo, giving 26.0 g of the desired intermediate, mp 140°–142° C.

EXAMPLE 6

2-Hydrazino-3a,4,5,6,7,7a-hexahydrobenzimidazole, hydrobromide 3a,4,5,6,7,7a-Hexahydro-2-thiobenzimidazole, hydrobromide was prepared by the method of S. Huny and F. Muller, Ann. 651, 89 (1962).

A 31.2 g portion of the above compound in a solution of 25 ml of ethyl bromide and 200 ml of ethanol was refluxed for 8 hours, then clarified and cooled to −10° C. The mixture was added to 800 ml of ether and cooled to dry-ice temperature. The resulting oily precipitate was collected and triturated with ether. The resulting crystals were collected, washed with ether and dried at 60° C. in vacuo, giving 40.2 g of 2-(ethylthio)3a,4,5,6,7,7a-hexahydrobenzimidazole, hydrobromide.

A 26.5 g portion of 2-(ethylthio)-3a,4,5,6,7,7a-hexahydrobenzimidazole, hydrobromide in 200 ml of ethanol was stirred and treated with 5.5 ml of hydrazine hydrate. The mixture was stirred on a steam bath for 16 hours, cooled to −10° C., added to 1600 ml of ether and cooled to 4° C. The oily precipitate was collected, washed with ether and dried at 60° C. in vacuo, giving 6.0 g of the desired intermediate, mp 195°–196° C.

EXAMPLE 7

2-(1-Methylhydrazino)-2-imidazoline, hydroiodide

A solution of 48.8 g of 2-methylthioimidazoline, hydroiodide, 10.0 g of methylhydrazine and 200 ml of ethanol was refluxed for several hours, then clarified and cooled to −10° C. The solid was collected, washed with ether and dried at 60° C. in vacuo, giving 33.4 g of the desired intermediate, mp 146°–147° C.

EXAMPLE 8

2-Hydrazino-1,4,5,6-tetrahydro-5-pyrimidinol, hydrobromide

A mixture of 26.4 g of tetrahydro-5-hydroxy-2(1H)-pyrimidinethione, 30 ml of ethyl bromide and 250 ml of ethanol was refluxed for 7 hours, clarified, diluted with 250 ml of ether and cooled to −10° C. The solid was crystallized twice from ether, giving 19.5 g of 2-(ethylthio)-1,4,5,6-tetrahydro-5-pyrimidinol, hydrobromide, mp 106°–108° C.

A mixture of 11.5 g of 2-(ethylthio)-1,4,5,6-tetrahydro-5-pyrimidinol, hydrobromide, 2.5 ml of hydrazine hydrate and 50 ml of ethanol was stirred at reflux for 5 hours, taken to dryness in vacuo and suspended in 100 ml of 2-propanol at the boil. A 100 ml portion of methanol was added at the boil, then the solution was clarified and cooled to −10° C., giving 4.9 g of the desired intermediate, mp 163°–164° C.

EXAMPLE 9

2,5-Dihydro-3-hydrazino-1H-2,4-benzodiazepine, hydroiodide 2,5-Dihydro-3-(methylthio)1H-2,4-benzodiazepine, hydroiodide was prepared by the method of Elslager, et. al., J. Het. Chem., 5, 609 (1968).

A mixture of 7.5 g of the above compound, 1.5 g of hydrazine hydrate and 100 ml of ethanol was refluxed for 8 hours, clarified and 100 ml of ether was added at the boil. The mixture was cooled and the solid collected, washed with ether and dried at 60° C. in vacuo, giving 5.7 g of the desired intermediate, mp 182°–183° C.

EXAMPLE 10

2-Hydrazino-4,4-diphenyl-2-imidazoline, hydrobromide

A mixture of 9.4 g of 4,5-diphenyl-2-thio-2-imidazoline, 5 ml of ethyl bromide and 250 ml of ethanol was stirred at reflux for 16 hours, then cooled to −10° C., 7 volumes of ether were added and the mixture was cooled to 4° C. The solid was collected, washed with ether and dried at 60° C. in vacuo, giving 2-(ethylthio)-4,4-diphenyl-2-imidazoline, hydrobromide.

A mixture of 6.8 g of the above compound, 1.2 g of hydrazine hydrate and 100 ml of ethanol was stirred at reflux for 20 hours, clarified while hot and the filtrate dilute with 200 ml of ether and cooled to −10° C. The solid was collected, washed with ether and dried at 60° C. in vacuo, giving 5 g of the desired intermediate, mp 227°–228° C.

EXAMPLE 11

4,5,6,7-Tetrahydro-2-hydrazino-4,4,7,7-tetramethyl-1H-1,3-diazepine, hydroiodide A 72 g portion of 2,5-diamino-2,5-dimethylhexane was dissolved in 750 ml of ethanol. This solution was stirred at <10° C. as 50 g of carbon disulfide was added during 15 minutes. After standing at room temperature 3 hours, the solid was collected, washed with ethanol then ether and air dried. A 25 g portion of this crude solid was added to 152 ml of methyl cellosolve, refluxed for 2 hours, treated with charcoal, clarified while hot and then cooled to −10° C. The solid was collected, washed with cold 2-propanol, then ether and dried at 60° C. in vacuo, giving 10.9 g of 4,5,6,7-tetrahydro-4,4,7,7-tetramethyl-2-thio-1H-1,3-diazepine, mp 226°–228° C.

A mixture of 18.6 g of 4,5,6,7-tetrahydro-4,4,7,7-tetramethyl-2-thio-1H-1,3-diazepine, 10 ml of methyl iodide and 150 ml of ethanol was stirred at reflux for 4 hours, clarified and cooled at −10° C. The solid was removed by filtration and the filtrate diluted to 400 ml with ether. This solution was concentrated at −10° C., giving a solid which was collected, washed with ether and dried at 60° C. in vacuo, giving 16.7 g of 4,5,6,7-tetrahydro-4,4,7,7-tetramethyl-2-methylthio-1H-1,3-diazepine, hydroiodide, mp 200°–205° C.

A 10.0 g portion of 4,5,6,7-tetrahydro-4,4,7,7-tetramethyl-2-methylthio-1H-1,3-diazepine, hydroiodide was dissolved in 150 ml of ethanol and 2.5 g of hydrazine was added. The mixture was refluxed 6 hours, diluted with 300 ml of ether and stored at −10° C. The solid was removed by filtration. The filtrate was concentrated to about 25 ml in vacuo, diluted with 50 ml of 2-propanol, then 200 ml of ether and stored at −10° C. The solid was collected, washed with ether and dried in vacuo at 60° C., giving 3.5 g of the desired intermediate, mp 154°–155° C.

EXAMPLE 12

7-Hydrazino-3,4,5,6-tetrahydro-2H-azepine

A 22.5 g portion 7-methoxy-3,4,5,6-tetrahydro-2H-azepine was reacted with 11.3 g of hydrazine hydrate in 200 ml of ethanol by the procedure of Example 9, giving the desired intermediate.

EXAMPLE 13

2-Hydrazino-3,4,5-tetrahydropyridine

A reaction mixture comprising 25 g of 97% S-valerolactam, 50 g of Lawesson's reagent and 150 ml of toluene was heated at 110° C. overnight. The reaction mixture was poured, while hot, into a sintered glass funnel prepared with N,N-aluminium oxide neutral, with a filter paper on top. The funnel was washed with one liter of methylene chloride and the filtrate and was evaported to dryness. The residue was triturated with ether, filtered and the residue dried, giving 14.26 g of 2-piperidinethione.

An 11.5 g portion of 2-piperidinethione was slurried in 120 ml of acetone, filtered and the filtrate treated with 15.1 g of methyl iodide. The solid was collected and dried, giving 8.85 g of 3,4,5,6-tetrahydro-2-(methylthio)-pyridine hydroiodide.

A 6.43 g portion of 3,4,5,6-tetrahydro-2-(methylthio)-pyridine, hydroiodide was added to an ice-cold solution of 1.25 ml of hydrazine hydrate in 35 ml of ethanol. The suspension was stirred at ice bath temperature for 30 minutes, then the solid was collected, washed with ethanol and ether and dried, giving 3.5 g of 2-hydrazino-3,4,5,6-tetrahydropyridine, hydroiodide, which was converted to the monohydronitrate by treatment with silver nitrate in water.

EXAMPLE 14

7-(2-Methylhydrazino)-3,4,5,6-tetrahydro-2H-azepine

A solution of 1-aza-2-methoxy-1-cycloheptene, 13.3 ml of methylhydrazine and 200 ml of ethanol was refluxed overnight and then evaporated, giving the desired intermediate as an oil.

EXAMPLE 15

Hexahydrophenylhydrazine-2H-azepin-2-one, hydrochloride

A solution of 25.44 g of 1-aza-2-methoxy-1-cycloheptene, 25.4 ml of phenylhydrazine and 200 ml of ethanol was refluxed overnight and then evaporated to an oil. The oil was diluted with methanol and adjusted to pH 4.5 with concentrated hydrochloric acid. The solid was collected, slurried in 200 ml of chloroform and the solid collected, giving 19.5 g cf the desired intermediate mp 256°–260° C.

EXAMPLE 16

5-Hydrazino-3,4-dihydro-2H-pyrole

2-Pyrrolidone was reacted with Lawesson's reagent in toluene as described in Example 13, giving 2-pyrrolidonethione, which was then reacted with methyl iodide by the procedure of Example 13, giving 3,4-dihydro-5-methylthiopyrrolidone hydroiodide which was reacted with hydrazine hydrate in ethanol, giving the desired intermediate, mp 127°–130° C.

EXAMPLE 17

2-Hydrazino-4,5-dihydro-1H-imidazole compound with platinum chloride (1:1)

To a solution of 4.16 g of potassium tetrachloroplatinate in 15 ml of water was added a 15 ml aqueous solution containing 1.37 g of 2-hydrazino-4,5-dihydro-1H-imidazole and 0.82 g of sodium acetate. The mixture was allowed to stand at room temperature for 24 hours to give the desired complex as light brown crystals mp>290° C.

EXAMPLE 18

2-Hydrazino-4,5-dihydro-α-methyl-1H-imidazole-1-ethanol, compound with platinum chloride (1:1)

To a solution of 858.4 mg of 2-hydrazino-α-methyl-2-imidazoline-1-ethanol, hydroiodide in 10 ml of water was added a solution of 1.245 g of potassium tetrachloroplatinate in 10 ml of water. A 5 ml portion of N,N-dimethylformamide was added, the mixture was stirred overnight and then filtered. The filtrate was diluted with water and the solid filtered and dried, giving 370 mg of the desired product, mp>300° C.

Following the procedure of Example 18 and using the intermediates of Examples 2-16, the products of Examples 19-32, listed in Table II, were obtained.

TABLE II

| Example | Intermediate | Product | MP °C. |
|---|---|---|---|
| 19 | 2 | 2-hydrazino-1,4,5,6-tetrahydropyrimidine compound with platinum chloride (1:1) | >300 |
| 20 | 3 | 2-hydrazino-4,5,6,7-tetrahydro-1H—1,3-diazepine, compound with platinum chloride (1:1) | >300 |
| 21 | 4 | 2-hydrazino-1,4,5,6-tetrahydro-5,5-dimethyl-pyrimidine compound with platinum chloride (1:1) | >300 |
| 22 | 6 | 2-hydrazino-3a,4,5,6,7,7a-hexahydro-1H—benzimidazole, compound with platinum chloride (1:1) | >280 |
| 23 | 7 | 4,5-dihydro-2-(1-methylhydrazino)-1H—imidazole, compound with platinum chloride (1:1) | >290 |
| 24 | 8 | 2-hydrazino-1,4,5,6-tetrahydro-5-pyrimidinol, monohydrobromide, compound with platinum chloride (1:1) | >300 |
| 25 | 9 | 3-hydrazino-2,5-dihydro-1H—2,4-benzodiazepine, compound with platinum chloride | >300 |
| 26 | 10 | 2-hydrazino-4,5-dihydro-4,4-diphenyl-1H—imidazole, compound with platinum chloride (1:1) | >270 |
| 27 | 11 | 2-hydrazino-4,5,6,7-tetrahydro-4,4,7,7-tetramethyl-1H—1,3-diazepine compound with platinum chloride (1:1) | >300 |
| 28 | 12 | 7-hydrazino-3,4,5,6-tetrahydro-2H—azepine, compound with platinum chloride (1:1) | >200 |
| 29 | 13 | 2-hydrazino-3,4,5,6-tetrahydropyridine, compound with platinum chloride (1:1) | 170 (dec) |
| 30 | 14 | 7-(1-methylhydrazino)-3,4,5,6-tetrahydro-2H—azepine, compound with platinum chloride (1:1) | 235 (dec) |
| 31 | 15 | hexahydrophenylhydrazone-2H—azepin-2-one, monohydrochloride, compound with platinum chloride (1:1) | 120 (dec) |
| 32 | 16 | 5-hydrazino-3,4-dihydro-2H—pyrrole, compound with platinum chloride (1:1) | 220 |

EXAMPLE 33

4,5-Dihydro-2-(2-methylhydrazino)-1H-imidazole, compound with platinum iodide (1:1)

A 12.2 g portion of 2-methylthioimidazoline, hydroiodide was dissolved in 30 ml of ethanol. A 5.32 ml portion of methyl hydrazine was added dropwise over ½ hour. This mixture was refluxed overnight, then chilled in an ice bath. The solvent was evaporated and the residue triturated with ether and refrigerated overnight. The mxture was evaporated to an oil which was dissolved in methanol and added to 400 ml of ether. The resulting solid was collected, dissolved in hot methanol and poured into 100 ml of ether. The resulting solid was collected, giving 4,5-dihydro-2-(2-methylhydrazino)-1H-imidazole, hydroiodide.

To a 1.0 g portion of the above compound in 50 ml of water was added 223 mg of sodium methoxide followed by a solution of 1.7 g of potassium tetrachloroplatinate in water. The mixture was stirred overnight and the product collected, giving 1.6 g, mp>320° C.

EXAMPLE 34

4,5-Dihydro-2-[2-(2,2,2-trifluoroethyl)hydrazino]-1H-imidazole, compound with platinum iodide (1:1)

To a solution of 12.2 g of 2-methylthioimidazoline, hydroiodide in 30 ml of ethanol was slowly added 12.6 g of 2,2,2-trifluoroethyl hydrazine, dropwise over 30 minutes. This mixture was refluxed overnight, then evaporated to an oil which crystallized on standing, giving 4,5-dihydro-2-[2-(2,2,2-trifluoroethyl)hydrazino]-1H-imidazole, hydroiodide, a one gram portion of which was reacted as described in Example 33, giving 1.0 g of the desired product, mp>290° C.

EXAMPLE 35

Preparation of Dinitro Derivatives

To a suspension of 1 m mole of a dichloride derivative, selected from those of Examples 17-32, in 50 ml of water is added 2 m moles of silver nitrate. The mixture is stirred at room temperature for 3 hours and then filtered. The filtrate is evaporated to dryness, giving the desired dinitro derivatives of formula I, where X and X' are $NO_2$.

To obtain the organic acid derivatives the dinitro derivative is stirred with one molar equivalent of the potassium salt of a dibasic acid or two molar equivalents of the potassium salt of a monobasic acid in an aqueous medium.

We claim:
1. A compound of the formula:

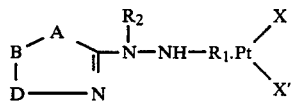

wherein $R_1$ is hydrogen, alkyl($C_1$–$C_6$), trifluoroethyl or phenyl; $R_2$ is hydrogen or alkyl($C_1$–$C_6$); A is a moiety of the formulae —S—, —O—, —$CH_2$— or

wherein $R_3$ is hydrogen or 1-methylethanol; —B—D— is a divalent moiety selected from the group consisting of those of the formulae:

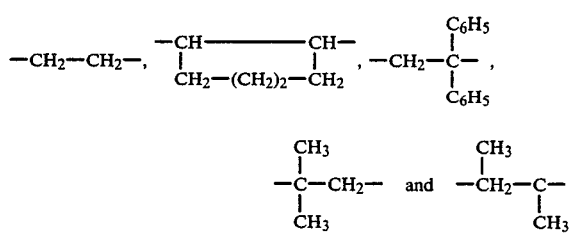

and X and X' are the same or different and are selected from the group consisting of halide, nitrate, nitrite, thiocyanate, sulfate and a monobasic organic acid and X and X' taken together is a dibasic organic acid.

2. The compound according to claim 1; 2-hydrazino-4,5-dihydro-α-methyl-1H-imidazole-1-ethanol, compound with platinum chloride (1:1).

3. The compound according to claim 1; 4,5-dihydro-2-(1-methylhydrazino)-1H-imidazole, compound with platinum chloride (1:1).

4. The compound according to claim 1; 2-hydrazino-4,5-dihydro-4,4-diphenyl-1H-imidazole, compound with platinum chloride (1:1).

5. The compound according to claim 1; 4,5-dihydro-2-(2-methylhydrazino)-1H-imidazole, compound with platinum iodide (1:1).

6. The compound according to claim 1; 2-hydrazino-4,5-dihydro-1H-imidazole compound with platinum chloride (1:1).

7. The compound according to claim 1; 2-hydrazino-3a,4,5,6,7,7a-hexahydro-1H-benzimidazole, compound with platinum chloride (1:1).

8. The compound according to claim 1; 5-hydrazino-3,4-dihydro-2H-pyrrole, compuond with platinum chloride (1:1).

9. The compound according to claim 1; 4,5-dihydro-2-[2-(2,2,2-trifluoroethyl)hydrazino]-1H-imidazole, compound with platinum iodide (1:1).

* * * * *